United States Patent [19]

Kusumi et al.

[11] 4,339,588
[45] Jul. 13, 1982

[54] PLANT GROWTH REGULATORS COMPRISING 4-HYDROXYISOXAZOLE AND RELATED COMPOUNDS

[75] Inventors: Takenori Kusumi; Koji Nakanishi, both of New York, N.Y.

[73] Assignee: Suntory Limited, Osaka, Japan

[21] Appl. No.: 277,593

[22] Filed: Jun. 26, 1981

Related U.S. Application Data

[62] Division of Ser. No. 195,748, Oct. 10, 1980, abandoned.

[51] Int. Cl.$^3$ .......................................... C07D 261/08
[52] U.S. Cl. .................................. 548/247; 548/243; 71/88
[58] Field of Search .......................................... 548/247

[56] References Cited

PUBLICATIONS

Sanai, et al., Chemical Abstracts, vol. 91, 187855(b).
DeKimpe et al., Chemical Abstracts, vol. 83, 97100(g).

Primary Examiner—Glennon H. Hollrah
Assistant Examiner—Sharon A. Gibson
Attorney, Agent, or Firm—Wyatt, Gerber, Shoup, Scobey & Badie

[57] ABSTRACT

The compound 4-hydroxyisoxazole and its lower alkyl and acyl derivatives are useful as plant growth regulators, particularly as herbicides.

3 Claims, No Drawings

PLANT GROWTH REGULATORS COMPRISING 4-HYDROXYISOXAZOLE AND RELATED COMPOUNDS

This is a division of application Ser. No. 195,748 filed Oct. 10, 1980, now abandoned.

This invention is concerned with the field of plant growth regulators. More specifically, it is concerned with certain 4-substituted isoxazoles useful for the prevention of germination of seeds of unwanted plant species, and with agriculturally useful compositions containing them.

The compounds of the invention may be represented by the formula:

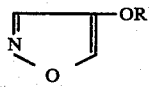

wherein R is hydrogen; lower acyl containing, for example, up to six carbon atoms; lower alkyl containing, for example, up to six carbon atoms; and substituted and unsubstituted phenyl and benzyl. Substituents, if present on a phenyl or benzyl group will be reaction inert, that is, they will not interfere with the preparation of the desired compound. Typical substituents include, for example, one or more alkyl groups containing up to five carbon atoms, cyano, and halogen.

The invention is also concerned with novel tertiary alcohols used for the preparation of the agriculturally useful products of the invention.

The compound 4-hydroxy isoxazole may be prepared from the known compound 4-isoxazole carboxylic acid by a reaction sequence in which the acid is converted to an acid halide, preferably a chloride or bromide and then to a tertiary alcohol by the Grignard reaction. Oxidation of the alcohol yields the desired compound.

The novel tertiary alcohols of the invention may be represented by the formula:

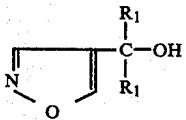

wherein $R_1$ is lower alkyl, preferably methyl or ethyl.

Conversion of the carboxylic acid to the corresponding acid halide may be effected by reaction with thionyl halide or with a phosphorous tri- or pentahalide. The preferred halides for use in the preparation of the acid halide are chlorides since they afford good yields and are available at reasonable costs. The corresponding bromides, fluorides and iodides are generally more expensive and, in some cases, less reactive. The presently preferred chloride reagent is phosphorous pentachloride. The use of this reagent results in good yields of high quality product which may be used in situ for direct conversion to the tertiary alcohol.

In the presently preferred reaction for the preparation of 4-isoxazolecarboxylic acid chloride, the acid is reacted with phosphorous pentachloride in a reaction inert organic solvent, suitably an aliphatic or aromatic solvent such as benzene or other hydrocarbon containing up to eight carbon atoms such as toluene or isooctane. A solvent is not essential, however.

Equimolar quantities of reactants may be employed, but often an excess of the phosphorous pentachloride, say up to 10% molar excess, will be employed to insure as complete a reaction as possible. Too large an excess should be avoided to limit purification problems.

The initial reaction is somewhat exothermic, and it is best to control the temperature so that the solvent does not boil to vigorously.

The reaction is usually complete in from 15 to 60 minutes at from 75° C. to 100° C. The acid chloride may be isolated, if desired, but it is preferred to remove the byproduct phosphorous oxychloride and proceed directly with the Grignard reaction. The oxychloride may be removed by distillation at reduced pressure.

The reaction for the formation of the tertiary alcohol takes place under Grignard conditions, that is, in a reaction inert, polar, organic solvent, at a temperature of from about −15° C., to 5° C., in an inert atmosphere during a period of from 1 to 4 hours. The preferred solvents are aliphatic or cycloaliphatic ethers and of these, diethyl is the most preferred. Nitrogen is preferred to insure an inert atmosphere although other dry inert gases such as helium can also be employed.

Generally, an excess of the Grignard reagent is employed to insure as complete a reaction as possible. As much as 150% to 300% molar excess may be used. Methyl or ethyl Grignard reagents will normally be employed since they are readily prepared and afford good yields.

The product can be isolated by any of the well known methods generally employed by those skilled in the art. One convenient procedure is to decompose the excess Grignard reagent with aqueous mineral acid, and to recover the product by extraction with, for example, ether. The product may be recovered from the solvent by removing the solvent at reduced pressure followed by chromatography, for example, over silica gel.

It is also possible to prepare the tertiary alcohol by reaction of the Grignard reagent with 4-isoxazolecarboxylic acid esters, for example, the ethyl ester with the Grignard reagent. The ester is prepared by reaction of ethyl alcohol with the corresponding acid which is then reacted with the Grignard reagent under the conditions described above. The method is not preferred, however, because the better yields are obtained working through the acid chloride.

The tertiary alcohol is next oxidized with a peroxide to produce the desired 4-hydroxyisoxazole. The reaction takes place under strongly acidic conditions at a temperature of from 30° C. to 50° C. during a period of from about 15 to 60 minutes. One convenient procedure is to oxidize with a combination of peroxide and sulfuric acid in a lower carboxylic acid to neutralize followed by extraction with ether and recover the desired product from the ether.

A solvent may be used. The presently preferred solvents are low boiling halohydrocarbons such as dichloromethylene or dichloroethylene.

A large molar excess of oxidizing reagent, say up to 200% molar excess or even higher, may be employed.

The ether and acylated derivatives within the scope of the formula first given above may be prepared by standard procedures.

The ethers are prepared by reaction between the hydroxy compound and the appropriate alkyl or aralkyl halide, preferably bromide or iodide, in a polar organic solvent suitably an ester or ketone containing up to eight carbon atoms, at from 25° C. to 40° C. during a period of 4 to 8 hours. The reaction is catalyzed by base, but a weak base such as an alkali metal carbonate or bicarbonate should be employed since the compounds are somewhat unstable in the presence of base. The methyl ether is conveniently prepared by reaction with diazomethane.

Acylated compounds are prepared by reaction between 4-hydroxyisoxazole and up to an eight molar excess of acylating agent, preferably an acyl chloride at from 25° C. to 40° C. for a period of from 30 minutes to two hours. The preferred solvent is pyridine since it functions both as a catalyst and a scavenging agent for the hydrogen halide which forms as a product of the reaction. The reaction may be improved by the addition of another basis reagent, preferably a nitrogenous organic base such as dimethylaminopyridine. It is, however, not necessary to do so.

The efficacy of the herbicidal products of this invention has been established utilizing the standard lettuce seed germination test.

The seed germination bioassay is carried out in two inch petri dishes. The fresh lettuce seeds are soaked in distilled water twelve hours before the test. The water is changed every hour for the first five hours.

For the preparation of the stock solution of the sample under test, 10 mg of the sample is first placed in a 10 ml volumetric flask. An appropriate solvent is added. Water is the preferred solvent, but a number of general organic solvents are also suitable.

On the bottom of the two inch petri dish is placed a piece of two inch No. 2 filter paper. If the stock solution is made of water, the general preparation of the bioassay sample at the desired concentration is as follows: X ml of the stock sample solution is added to the filter paper and y ml of water is added, as indicated in Table I to make the total volume of the aqueous solution equal to two ml. Two more pieces of filter papers are placed over the first, and the bioassay sample is ready for the test.

If the stock solution is made of organic solvent, then a different procedure is employed. The same amount of the stock solution, as in Table I is added to each petri dish for each desired concentration. The organic solvent is evaporated by blowing nitrogen gas over the filter paper. After all of the organic solvent is evaporated, two ml of distilled water and two pieces of filter paper are added to the dish. The dish is left standing at room temperature for 12 hours.

Twenty-five seeds are placed in each petri dish on top of the filter paper and the result of the germination inhibition is obtained after 48 hours by counting the germinated and non-germinated seeds. The activity is indicated by the percentage of seeds germinated in each dish, and is recorded in Table II.

TABLE I

| Concentration (ppm) | Xml (stock solution) | Yml (water) |
| --- | --- | --- |
| 1000 | 2 | 0 |
| 500 | 1 | 1 |
| 250 | 0.5 | 1.5 |
| 100 | 0.2 | 1.8 |
| 50 | 0.1 | 1.9 |

TABLE II

| Concentration (ppm) | Seeds Germinated Per 25 Seeds Tested |
| --- | --- |
| 1000 | 0 |
| 500 | 0 |
| 100 | 0 |
| 50 | 8 |
| 25 | 17 |
| 10 | 17 |
| 5 | 20* |
| 3 | 22* |

*Average of 3 runs

It will be seen from the above that the products of this invention have useful antigermination properties at concentrations as low as 50 ppm and under the conditions of the test are one hundred percent effective at concentrations of only 100 ppm. The most useful compositions of the invention, therefore will contain at least 0.005% by weight of active ingredients. Presently preferred compositions will contain from 0.005% to 0.01% by weight. Appreicable variation from this range however, may be acceptable. To prevent germination of some seeds, concentrations below 0.005% may be herbicidally effective, but for other seeds, concentrations above 0.01% may be desirable for best results. The amount of herbicidal compound in a composition containing a herbicidally effective amount of a compound of this invention may vary over an extremely wide range. This is attributable to the unexpectedly high order of activity of the compounds.

The compounds of the invention may be used alone, but because of their high order of activity will normally be used in association with a wide variety of agriculturally acceptable carriers which may be liquid, semisolid gels or solids. The compounds of the invention may also be distributed in aerosol form.

The products may be distributed in pure or relatively crude form, or in the form of concentrates all of which may be diluted for use by the retailer or by the ultimate consumer.

The products may be distributed in solutions, dispersions, suspensions or emulsions which may contain one or more surfactants. The liquid vehicle for such compositions may be water or any of a variety of hydrocarbon or other known agriculturally acceptable excipients. For large scale agricultural use, the preferred carrier is water or a relatively inexpensive hydrocarbon such as any of a variety of mixtures of low molecular weight, aliphatic hydrocarbons normally containing ingredients with up to eight carbon atoms. Several of these mixtures are available in the art.

For solid compositions such as dusts, the products may be dispersed on vermiculite, powdered walnut shells or any of a wide variety of solid carriers known to the art.

The products and compositions of the invention may be used following any of the usual procedures well known in the art. The growth of unwanted plants may be inhibited by contacting the seeds of the plant with a herbicidally effective amount of the selected agent in any of the various composition forms described above. The compositions may be sprayed, dusted or otherwise spread on the area to be treated.

The following non-limiting examples are given by way of illustration only.

EXAMPLE 1

4-(2-HYDROXYPROPAN-2-YL)ISOXAZOLE

Phosphorous pentachloride (8.78 g) is added to a solution of 4-isoxazolecarboxylic acid (4.77 g) in 15 ml of dry benzene in a 3-necked round bottom flask equipped with a nitrogen inlet, a stirrer and a reflux condenser protected with a calcium chloride drying tube. During the addition the temperature is maintained somewhat below the reflux temperature. It is then heated to reflux and stirring under reflux is continued for 30 minutes. The benzene and phosphorous oxychloride are removed under reduced pressure with an oil pump until the weight of the residue reaches 5.5 g (assumed 100% yield).

The residue is taken up in 120 ml of ether and the reaction flask flushed with nitrogen. To the solution is added 30.2 ml of 2.8 M methyl magnesium bromide (2 eq.) at $-15°$ C. The mixture is stirred at $-10°$ C. for two hours and poured slowly into 120 ml of 1 N hydrochloric acid to decompose excess Grignard reagent. The aqueous mixture is extracted three times with 20 ml portions of ether, and the extracts combined. The combined extracts are dried over anhydrous magnesium sulfate, filtered, dried, and the ether removed at reduced pressure to leave 3.65 g of oil. The oil is chromatographed on a silica gel column by passing over a column and eluting with 1:9 ethyl acetate-methylene dichloride to obtain the desired product upon evaporation of the solvent.

The compound 4-(3-hydroxypentan-3-yl)isoxazole is similarly prepared using ethyl magnesium bromide.

EXAMPLE 2

4-(2-HYDROXYPROPAN-2-YL)ISOXAZOLE

A solution of 2.80 g 4-isoxazolecarboxylic acid ethyl ester in 100 ml of dry ether is prepared in a 3-necked round bottom flask equipped with a nitrogen inlet, a stirrer and a reflux condenser protected with a calcium chloride drying tube. To this solution is added a Grignard reagent prepared from 970 mg of magnesium and 2.6 ml of methyl iodide in 40 ml of ether, under nitrogen, at $-10°$ C., with stirring during a period of one-half hour and stirring is continued for an additional one and one-half hour while a white precipitate forms. The mixture is then stirred at about 25° C. for an additional hour and poured into 100 ml of ice cold 1 N hydrochloric acid. The mixture is extracted with ether as in Example 1, and the extracts treated in the same manner to obtained the desired product.

EXAMPLE 3

4-HYDROXYISOXAZOLE

To a solution of 2.83 g of 4-(2-hydroxypropan-2-yl)isoxazole in dichloromethane is added an oxidizing reagent prepared by mixing 5 ml of 30% hydrogen peroxide and 6.5 ml of concentrated sulfuric acid at a rate to keep the dichloromethane at gentle reflux. The solution is neutralized with 5% aqueous sodium bicarbonate solution and extracted three times with 100 ml portions of ether. The extracts are combined, dried over anhydrous magnesium sulfate, filtered, and concentrated at reduced pressure to leave a solid residue. The residue is taken up in 5:1 methylene dichloride-ethyl acetate and chromatographed over silica gel. Evaporation of the solvent from the fractions provides the desired compound (mp 66°–67° C.).

EXAMPLE 4

4-HYDROXYISOXAZOLE

A solution containing 150 mg of 4-(2-hydroxypropan-2-yl)isoxazole, three drops of concentrated sulfuric acid, and 0.3 ml of tert-butyl hydroperoxide in 10 ml of acetic acid is allowed to stand at about 30° C. for 24 hours. The reaction mixture is diluted with 50 ml of water and neutralized by the addition of small portions of solid sodium carbonate. The mixture is extracted with four 50 ml portions of ether. The extracts are combined, dried over anhydrous magnesium sulfate, filtered, and evaporated under reduced pressure to provide a liquid residue. The residue is taken up in 10 ml of 65% sulfuric acid, allowed to stand at about 25° C. for 45 minutes, and the mixture neutralized by the addition of solid sodium carbonate in small portions. The mixture is extracted with four 20 ml portions of ether. The extracts are worked up as described above and evaporated to give an oil residue. The product is isolated from the oil as described in Example 3.

EXAMPLE 5

4-METHOXYISOXAZOLE

A diazomethane solution is prepared by adding 10 g of nitrosomethyl urea in small portions to 30 ml of 40% potassium hydroxide in 100 ml of ether. The temperature is maintained at from 0° C. to 5° C. during the addition. The ethereal solution turns yellow as the solid dissolves. The final mixture is stirred for about 15 minutes and the ether layer collected. The ether solution is dried over solid potassium hydroxide at 0° C. for three hours.

A total of 30 mg of 4-hydroxyisoxazole is added to the diazomethane solution which contains excess diazomethane and the mixture is allowed to stand at about 25° C. for six hours. The etheral solution is concentrated to about 25 ml at reduced pressure and passed through a short silica gel column. The impurities are adsorbed on the silica gel, and the extremely volatile product recovered in ether solution.

NMR-$\delta$(acetone-$D_6$) 8.50 (1H,s), 8.34 (1H,s), 3.80 (3H,s)

MS 100 (CI,M$^+$+1)

EXAMPLE 6

4-BENZYLOXYISOXAZOLE

A mixture containing 200 mg of 4-hydroxyisoxazole in 10 ml of acetone together with 1.5 equivalents of benzyl bromide and 1.5 equivalents of potassium carbonate is stirred at about 25° C. for five hours. The solid is filtered and the filtrate concentrated to an oil. The crude material is purified by chromatography on silica gel.

NMR $\delta$(CDCl$_3$) 8.19 (1H,s), 8.10 (1H,s), 7.3 (5H,br), 4.95 (2H,s)

The corresponding ethoxy, propoxy, and butoxy compounds are similarly prepared using ethyl iodide, propyl iodide and butyl bromide respectively.

The NMR spectra of these compounds are as follows:
4-Ethoxyisoxazole: $\delta$(CDCl$_3$) 8.1 (2H,br), 4.0 (2H,q), 1.4 (3H,t)
4-Propoxyisoxazole: $\delta$(CDCl$_3$) 8.1 (2H,br), 3.9 (2H,t), 1.6 (2H,m), 1.0 (3H,t)

4-Butoxyisoxazole: δ(CdCl₃) 8.1 (2H,br), 3.9 (2H,t), 1.6 (4H,m), (3H,t)

The procedure is also used to prepare analogs and homologs in which the benzyl moiety is substituted on the phenyl group with one or more chlorine, iodine, methyl or ethyl groups.

EXAMPLE 7

4-ACETOXYISOXAZOLE

A solution containing 11 mg 4-hydroxyisoxazole, 3 mg dimethylaminopyridine, 0.3 ml pyridine and two drops of acetic anhydride is stirred at about 25° C. for 24 hours. The reaction mixture is washed with 1 N HCl to remove the pyridine, and the aqueous layer extracted three times with 10 ml portions of ether. The etheral solution is washed with saturated aqueous sodium bicarbonate, dried over anhydrous magnesium sulfate, filtered and the ether removed under reduced pressure to give the desired product.

The corresponding propanoyl, butanoyl and pentanoyl compounds are similarly prepared.

The NMR spectra of the acetoxy compound has the following characteristics:

δ(acetone-D₆), 8.76 (1H,s), 8.34 (1H,s), 2.28 (3H,s)
MS 128 (CI, M⁺+1)
In the infrared there is a peak at 1770 Cm⁻¹

EXAMPLE 8

Solid Composition

A herbicidal composition is prepared by thoroughly mixing 4-hydroxyisoxazole and vermiculite at a concentration level of 100 ppm active ingredient.

EXAMPLE 9

Liquid Composition

A herbicidal composition is prepared by taking up 4-methoxyisoxazole at a concentration level of 90 ppm in hexane.

What is claimed is:

1. A compound of the group represented by the formula:

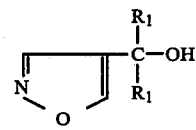

wherein R₁ is methyl or ethyl.
2. 4-(2-Hydroxypropan-2-yl)isoxazole.
3. 4-(3-hydroxypentan-2-yl)isoxazole.

* * * * *